United States Patent
Duret

(10) Patent No.: US 6,434,411 B1
(45) Date of Patent: Aug. 13, 2002

(54) METHOD FOR MEASURING A CONDUCTIVE VOLUME AND DEVICE FOR IMPLEMENTING THIS METHOD

(75) Inventor: Denis Duret, Grenoble (FR)

(73) Assignee: Commissariat A l'Energie Atomique, Paris (FR)

( * ) Notice: Subject to any disclaimer, the term of this patent is extended or adjusted under 35 U.S.C. 154(b) by 0 days.

(21) Appl. No.: 09/242,919

(22) PCT Filed: Aug. 29, 1997

(86) PCT No.: PCT/FR97/01536
§ 371 (c)(1),
(2), (4) Date: Feb. 25, 1999

(87) PCT Pub. No.: WO98/08435
PCT Pub. Date: Mar. 5, 1998

(30) Foreign Application Priority Data

Aug. 30, 1996 (FR) .............................................. 96 10632

(51) Int. Cl.⁷ ................................................. A61B 5/05
(52) U.S. Cl. ........................ 600/407; 800/409; 800/467; 800/487; 800/483; 800/486; 324/207.17; 73/861.17
(58) Field of Search ................................. 600/347, 409, 600/462–486; 324/207.17; 73/861.17, 861.67

(56) References Cited

U.S. PATENT DOCUMENTS

| | | | |
|---|---|---|---|
| 3,980,076 A | * | 9/1976 | Wikswo, Jr. et al. ....... 600/409 |
| 4,432,369 A | | 2/1984 | Halvorsen |
| 4,674,518 A | | 6/1987 | Salo |
| 4,686,987 A | | 8/1987 | Salo et al. |
| 4,958,638 A | * | 9/1990 | Sharpe et al. ............ 128/653.1 |
| 5,197,467 A | | 3/1993 | Steinhaus et al. |
| 5,210,490 A | * | 5/1993 | Munch et al. ......... 324/207.17 |

FOREIGN PATENT DOCUMENTS

| | | |
|---|---|---|
| EP | 0 112 248 | 6/1984 |
| EP | WO95/26677 | 10/1995 |

* cited by examiner

Primary Examiner—Marvin M. Lateef
Assistant Examiner—Jeoyuh Lin
(74) Attorney, Agent, or Firm—Anderson Kill & Olick, PC; Eugene Lieberstein; Michael N. Meller

(57) ABSTRACT

This invention relates to a process for measuring at least one dimension of a conducting volume, in which a measurement sensor (10) is placed in a cavity existing inside an homogeneous conducting or non-conducting body (11), the dimensions and resistivity of this cavity being large compared with the dimensions and resistivity of the volume to be measured, the characteristics of the sensor varying as a function of the immediate volume surrounding it, this medium being a medium with electromagnetic losses.

It also relates to a device for embodiment of this process.

14 Claims, 3 Drawing Sheets

METHOD FOR MEASURING A CONDUCTIVE VOLUME AND DEVICE FOR IMPLEMENTING THIS METHOD

TECHNICAL DOMAIN

This invention relates to a process for measuring a conducting volume and a device for using this process, this volume being placed in an homogeneous conducting body which is itself placed in an environment which has large dimensions and resistivity compared with the dimensions and resistivity of the volume to be measured.

STATE OF PRIOR ART

The rest of the description will refer to an example consisting of a device for measuring the heart rate making use of implanted sensors.

This type of device is used for the detection of irregularities in the heart rate and for the control of stimulators in a number of pathologies, or to determine the activity state of a patient.

Many parameters related to heart activity are measured, and in particular the partial pressure of oxygen in the blood, the mechanical measurement of contraction, measurement of the blood flow, direct measurement of electric activity (ECG) by electrodes, measurement of the blood pressure, measurement by the Doppler effect, measurement of the acceleration, etc.

The publications described below, the references of which are given at the end of the description, describe various embodiments according to prior art.

Reference [1] describes a system for monitoring the movement quantity or speed of cardiac masses by the use of an implanted sensor, this sensor being fixed to the internal muscular wall of the heart. Accelerometers, for example piezo-electric accelerometers, may be used as sensors.

Reference [2] describes a stimulation device including an accelerometric sensor and an electrode.

Reference [3] uses mechanical deformation sensors based on propagation lines, the impedance of which varies as a function of their geometry.

Reference [4] describes a system for measuring the velocity using a catheter comprising at least two staged electrodes. These electrodes form a polarized galvanic cell sensitive to the blood flow.

Reference [5] presents a system based on measuring the partial pressure of oxygen by electrodes.

Methods of measuring variations of the heart rate activity according to prior art do not use information about the global volume of a heart cavity. This magnitude is an extremely interesting marker, since the ejection volume may vary from 20 to 60% each time the heart beats. Furthermore, arrhythmia problems and other pathologies appear to be directly related to monitoring of this magnitude.

The purpose of this invention is a process for measuring this type of conducting volume.

DESCRIPTION OF THE INVENTION

This invention relates to a process for measuring at least one dimension of a conducting volume, characterized in that a measuring sensor is placed inside an existing cavity inside an homogeneous conducting or non-conducting body, the dimensions and resistivity of this cavity being large compared with the dimensions and resistivity of the volume to be measured, the sensor having characteristics that vary as a function of the medium immediately surrounding it. For example, the measurement sensor may include a self inductance mutually coupled to the medium, which may be a medium with electromagnetic losses.

The volume to be measured may vary with time.

In the first example embodiment, the process according to the invention is used for measuring the volume of a heart cavity which varies with variations in the heart cycle. Advantageously, the sensor may be placed at the end of a catheter which may consist of a coaxial transmission line.

In this example embodiment, the process according to the invention compares the normal cycle and the difference from the normal in order to detect any more or less serious dysfunctions in real time and in situ.

In a second embodiment, the process according to the invention is used to measure the diameter of a pipe with cylindrical geometry, for example such as a blood vessel.

The process according to the invention may then be coupled to a velocity measurement to measure the blood flow inside this vessel, this flow being an essential magnitude for evaluating cardiovascular pathologies.

More generally, the invention may be applied to any volume or diameter measurement of a pipe, provided that there is a contrast between the resistivity of the volume to be measured or the pipe and the resistivity of the surrounding medium.

The invention also concerns a device for embodiment of this process in which the measurement sensor comprises a self-inductance wound with adjacent or non-adjacent turns, and readout electronics comprising the following in sequence:

a 3 dB coupler receiving sensor data as input;

an amplifier;

a detection circuit, an amplifier being connected to this circuit and to the coupler;

a low-pass filter;

a shaping circuit connected to a signal output.

DETAILED DESCRIPTION OF EMBODIMENTS

Figure 1:
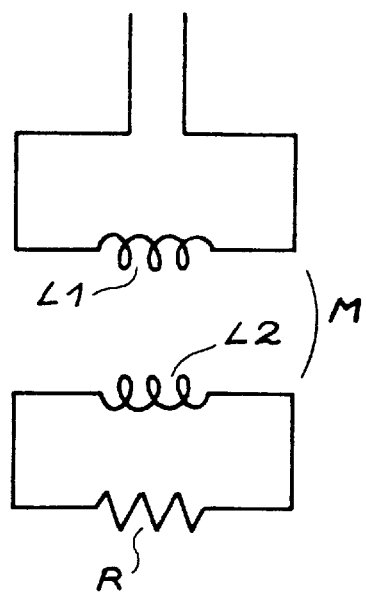
FIG. 1 illustrates the electrical equivalent of a device for embodiment of the process according to the invention.

The process according to the invention uses a sensor, the characteristics of which vary as a function of the immediate volume surrounding it, which may be a medium with electromagnetic losses. For example, the sensor may be a self-inductance mutually coupled to the medium. If the volume is variable, the coupling coefficient and the losses in the secondary circuit formed by the blood medium in this case, are variable and are directly related to variations in the volume. FIG. 1 shows the electrical equivalent of this type of device in which:

L1: measurement L

L2: L for the medium

R: losses

M: coupling coefficient.

Medium losses may be resistive or dielectric. They are mostly resistive for an application for measuring a heart cavity, and at the frequencies that are considered as an example (typically below 100 MHz).

Figure 2:
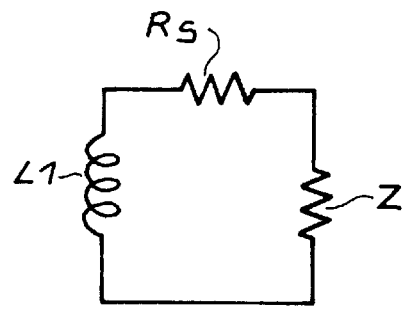
FIG. 2 illustrates the equivalent effect of the medium.

FIG. 2 shows the effect of the impedance of the medium corrected to the primary measurement circuit, where:

L1: measurement L $R_s$: series R (measurement)

Z: corrected Z

The equations of the coupled circuits are used to connect Z to L2 and to R using the following formula:

$$Z = \frac{\varpi^2 M^2}{R + jL2\varpi}$$

where R represents the intrinsic losses of the measurement inductance.

Figure 3:
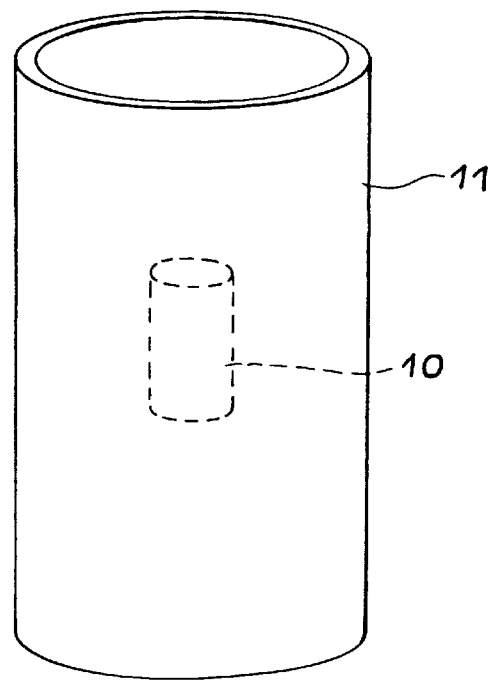
FIG. 3 illustrates a rudimentary example embodiment for using the process according to the invention.

FIG. 3 shows a rudimentary embodiment for using the process according to the invention, the measurement inductance being a self-inductance with a cylindrical geometry and the measurement volume being a conducting cylinder.

The measurement self-inductance 10 has a diameter d, length l, and the medium with losses 11, with conductivity σ, occupies the entire volume limited by the cylinder with diameter D and length L.

Volume variations in the cylinder limiting the conducting medium act on the inductance L2, on the R term and on the mutual term M; therefore they create an effect on the impedance in series with the measurement inductance. This effect becomes zero if the external medium has the same conductivity σ. It increases as the contrast in the resistivity between the variable volume cylinder and the external medium increases.

The frequency at which the impedance is measured is related to the measurement influence domain (in this case the diameter D); the influence diameter reduces as the frequency increases.

Figure 4A:
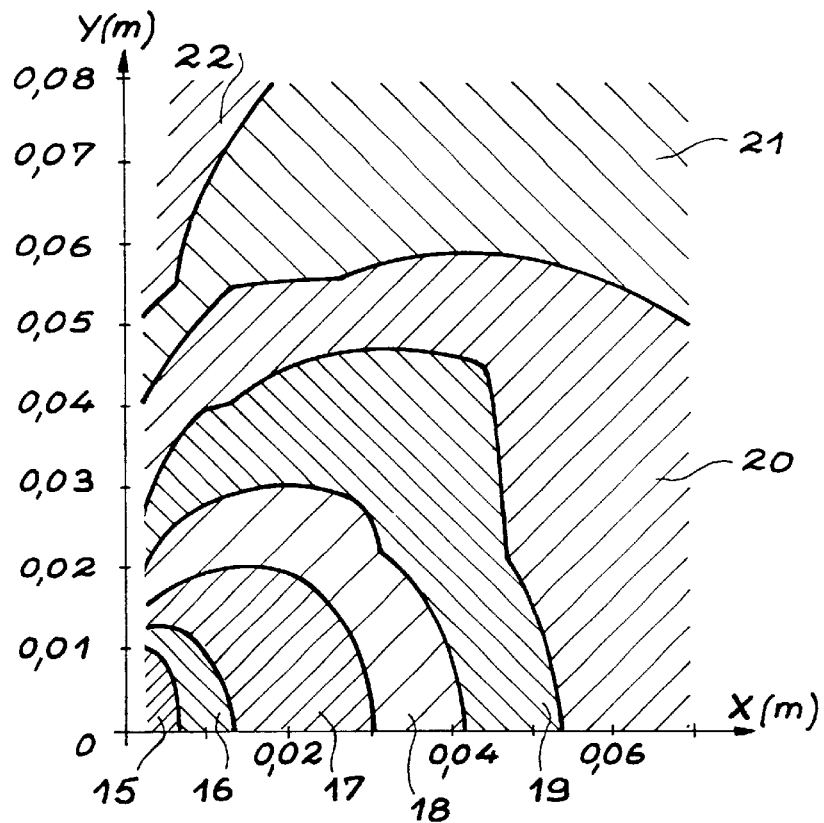
FIGS. 4A and 4B represent a simulation result.
Figure 4B:
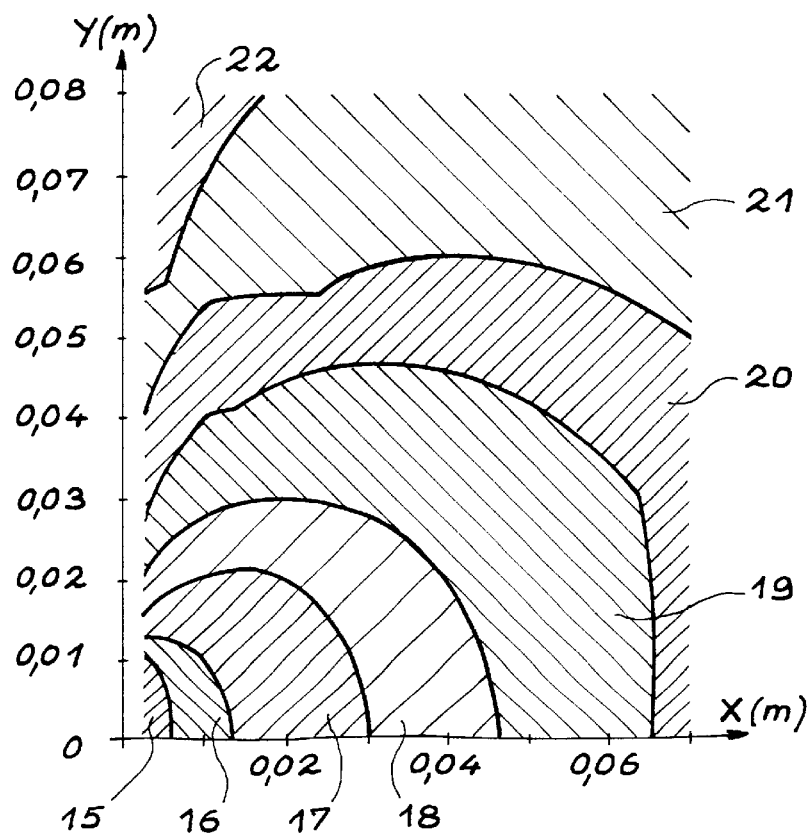

FIGS. 4A and 4B show a realistic simulation result for which the working frequency f (ω=2πf) is 10 MHz, the conductivities of the variable cylinder and of the external medium are 0.7 S/m and 0.1 S/m respectively. The plots show the magnetic energy in relative units for two geometric cases: D=6 and 10 cm, L=8 cm, d=5 mm, l=15 mm. A surrounding medium with an intermediate conductivity was considered. The dimensions and conductivity approximately represent a heart cavity full of blood, the heart muscle and lungs. These FIGS. 4A and 4B represent the variation in magnetic energy by simulation. The total magnetic energy varies by 2.8% between the two geometric cases, which corresponds approximately to the variations that could be expected on the corrected impedance. FIG. 4A represents a 3 cm heart with the following ranges:

15: −9 to −8
16: −10 to −9
17: −11 to −10
18: −12 to −11
19: −13 to −12
20: −14 to −13
21: −15 to −14
22: −16 to −15

FIG. 4B represents a 5 cm heart, with ranges identical to those in FIG. 4A being marked with the same references.

In one example embodiment, the invention proposes a process for globally measuring variations in the volume of a heart cavity, using its electromagnetic influence on an inductance placed in the cavity. These variations modify the apparent impedance of the measurement inductance. They may be demonstrated by conventional bridge or reflectometry means and may be picked up at the end of cable with a constant characteristic impedance, after matching.

The invention has many advantages. The measured parameter is global. It is purely geometric, and apparently has not been used specifically for applications in implanted heart monitoring. The sensor preferably used at the end of a catheter, for example with the catheter consisting of a coaxial transmission line, is particularly simple and robust (in this case, the length of the line is unimportant). Its influence with the medium is completely electromagnetic and therefore contact free.

Furthermore, any physiological coating reaction hardly disturbs the measurement since it only slightly modifies the geometric parameters of the coil. The measurement is completely innocuous; only a very low coupling energy with the medium is used (maximum of the order of 1 mW), at a frequency of the order of a few MHz. In the case of a conducting surrounding medium, the measurement device thus formed is self shielded; the surrounding conducting medium strongly attenuates propagation to the outside. Conversely, and for the same reason, this device is almost insensitive to surrounding electromagnetic disturbances.

We will now consider an example embodiment.

Figure 5:
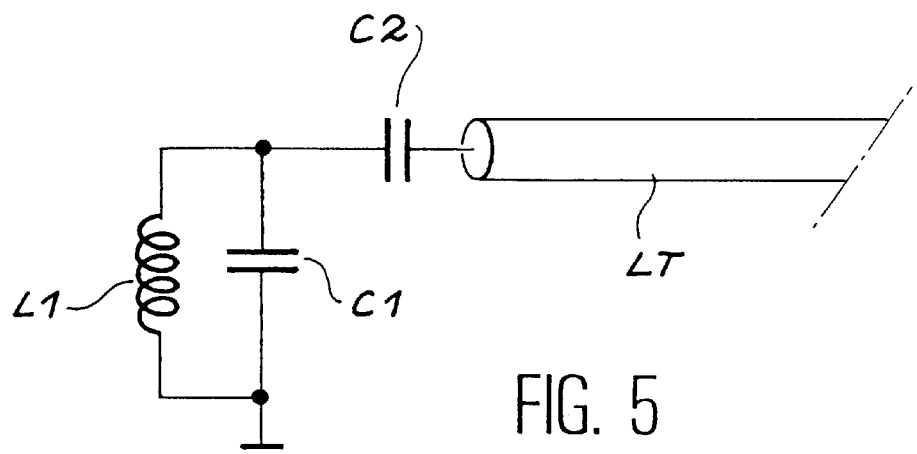
FIG. 5 illustrates a measurement of the impedance variation.

The measurement sensor comprises a 10 mm long and 2 mm diameter cylindrical self-inductance. It is wound with adjacent turns using 0.1 mm diameter copper wire. The value of the inductance for these parameters is of the order of 1.3 $\mu$H. The circuit in FIG. 5 shows a method of measuring impedance variations in which the resonant circuit may for example be matched at a frequency close to 10 MHz by a capacitance C1 of the order of 100 pF. This circuit is itself matched to the characteristic impedance of a transmission line LT, usually 50Ω, for example by a series capacitor C2. The value of this capacitance depends on intrinsic losses and losses through coupling, typically a few tens of a pF.

Figure 6:
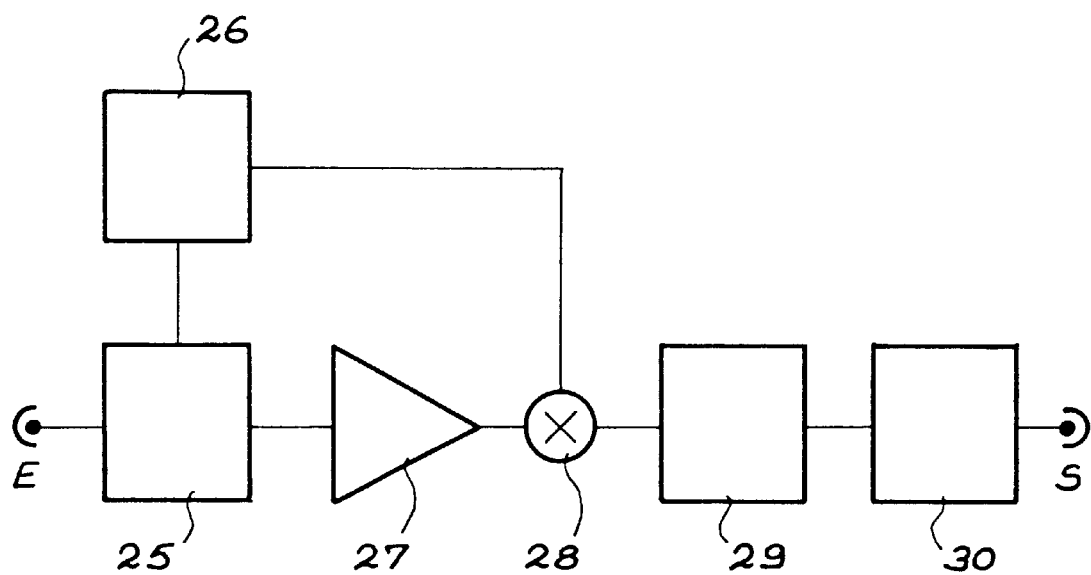
FIG. 6 illustrates electronics associated with the volume variation measurement sensor.

A bridge method may advantageously be used for the readout electronics, as shown in FIG. 6. This electronics comprises the following in sequence:

a 3 dB coupler 25, receiving input from the sensor E;

an amplifier 27;

a detection circuit 28, an amplifier 26 being connected to this circuit 28 and to the coupler 25;

a low-pass filter 29;

a shaping circuit 30 connected to a signal output S.

In this case, the bridge is a 3 dB coupler for which the output is zero when the load (the circuit extended by the line) is equal to 50Ω, and the value increases as the mismatch increases. The bridge is excited at the resonant frequency of the matched and adapted circuit. An amplifier accentuates the unbalance and a coherent, or envelope detection (case in the figure) is used to extract the mismatch information which is filtered and shaped, and is then used to determine the volume variation information.

As mentioned above, in a first industrial application the invention relates to the evaluation of variations in the volume of one of the heart cavities of a patient during a cycle. The volume of a heart cavity, or ventricle, can vary with variations in the heart cycle (systole and diastole); the ejected volume may vary from 20 to 60% in each beat. Contrasts in the resistivity between the heart cavity and the muscular tissue (2, 5), and between the heart cavity and the lung (14), make it possible to use the global variation in the liquid conducting blood (0.7 mhos/m) as a marker by measuring losses induced mutually with the sensor. Comparison with a normal cycle and the difference from the normal can be used to detect more or less serious dysfunctions in real time and in situ. Having detected these dysfunctions, it will be possible to act upon a stimulation device and possibly initiate defibrillation.

A second application relates to measuring the diameter of a pipe with cylindrical geometry; if the pipe is assumed to be long compared with the influence distance of the sensor, the sensor is sensitive to the average diameter of the pipe along its influence distance. In the health domain, this system is advantageously used for measuring the diameter of blood vessels. The device according to the invention may be coupled with a speed measurement based on a different principle to measure the blood flow, which is an essential magnitude in evaluating cardiovascular pathologies. Obviously, typical dimensions in this type of application are different, and also the operating frequency may advantageously be higher. The geometry, which helps to understand operation of this second application, is obtained by considering L as being infinite in FIG. 3.

Obviously, other applications of the invention could be envisaged in domains other than health.

REFERENCES

[1] EP-A-0 582 162 (SORIN BIOMEDICA)
[2] EP-A-0 515 319 (SORIN BIOMEDICA)
[3] WO 95/15784 (PACESETTER AB)
[4] WO 95/26677 (PACESETTER AB)
[5] U.S. Pat. No. 5,431,172 (PACESETTER AB)

What is claimed is:

1. A measurement sensing device for measuring at least one dimension of a conducting volume of a cavity inside a homogeneous body with said cavity representing a medium having electromagnetic losses, said measurement sensing device comprising a measurement sensor having an intrinsic self-inductance and being coupled by mutual inductance to said medium and an electrical readout circuit which comprises the following in sequence:

a 3 dB coupler receiving input from the sensor;

an amplifier;

a detection circuit, an amplifier being connected to this circuit and to the coupler;

a low-pass filter connected to said detection circuit; and a shaping circuit connected to said low-pass filter for outputting an output signal S.

2. A Device according to claim 1, which the self-inductance sensor is placed at the end of a catheter.

3. Device according to claim 2, in which the catheter comprises a coaxial transmission line.

4. A measurement sensing device as defined in claim 1, wherein said body in which the measurement is taken to a blood vessel and wherein said dimension to be measured is the diameter of the blood vessel.

5. A measurement sensing device as defined in claim 1, wherein said body in which the measurement is taken is a blood vessel and wherein the blood flow inside said blood vessel is being measured.

6. Device for measuring the volume of a heart cavity, which varies with variations in the heart cycle, comprising a measurement sensor placed inside this cavity, wherein the sensor includes characteristics that vary as a function of the medium immediately surrounding it.

7. Device according to claim 6, in which the measurement sensor has an intrinsic self-inductance and with said measurement sensor being coupled to said heart cavity by mutual inductance.

8. Device according to claim 6, in which the sensor is placed at the end of a catheter.

9. Device according to claim 8, in which the catheter consists of a coaxial transmission line.

10. Device according to claim 9, further comprising means for comparing the measured volume to variations in a normal heart cycle and means for measuring the differences from the normal cycle so that dysfunctions can be detected in real time.

11. Device according to claim 6, which the measurement sensor comprises a wound inductor having an intrinsic self-inductance and further comprising an electrical readout circuit which comprises the following, in sequence:

a 3 dB coupler receiving input from the sensor;

an amplifier;

a detection circuit, an amplifier being connected to this circuit and to the coupler;

a low-pass filter connected to said detection circuit; and a shaping circuit connected to said low-pass filter for outputting an output signal S.

12. A measuring sensing device for measuring at least one dimension of a conducting volume of a cavity inside a body, said volume being a medium with electromagnetic losses, said device comprising a sensor having an intrinsic self-inductance and being coupled by mutual inductance to said medium and an electrical readout circuit which comprises the following components in sequence: a 3 dB coupler receiving a signal from the sensor, a first amplifier connected to a first out of said coupler, a detection circuit having a first input connected to said first amplifier, a low-pass filter receiving the output signal from said detection circuit, a second amplifier being connected between a second output of the coupler and a second input of the detection circuit and a shaping circuit connected to the detection circuit for outputting a signal S.

13. A measurement sensing device for measuring the diameter of a blood vessel comprising a self-inductance wound sensor coupled by mutual inductance to the surrounding medium, and an electrical readout circuit, which comprises the following components in sequence: a 3 dB coupler receiving a signal from the sensor and providing a first and second output, a first amplifier connected to the first output of said coupler, a detection circuit having a first input connected to said first amplifier and a second input, a low-pass filter receiving the output signal from said detection circuit, a second amplifier being connected between the second output of the coupler and a second input of the detection circuit and a shaping circuit connected to the detection circuit for outputting a signal S.

14. A measurement sensing device for measuring the blood flow inside a blood vessel comprising a self-inductance would sensor coupled by mutual inductance to the surrounding medium, and an electrical readout circuit, which comprises the following components in sequence: a 3 dB coupler receiving a signal from the sensor, a first amplifier connected to a first output of said coupler, a detection circuit having a first input connected to said first amplifier, a low-pass filter receiving the output signal from said detection circuit, a second amplifier being connected between a second output of the coupler and a second input of the detection circuit and a shaping circuit connected to said detection circuit for outputting a signal S.

* * * * *